United States Patent [19]

Searle et al.

[11] 4,045,575
[45] Aug. 30, 1977

[54] THIOAMIDE PESTICIDES

[75] Inventors: Robert J. G. Searle, Sittingbourne; Clive B. C. Boyce, Herne Bay, both of England

[73] Assignee: Shell Oil Company, Houston, Tex.

[21] Appl. No.: 665,220

[22] Filed: Mar. 9, 1976

[30] Foreign Application Priority Data

Mar. 11, 1975 United Kingdom ............... 10070/75

[51] Int. Cl.$^2$ ..................... C07C 153/067; A01N 9/12
[52] U.S. Cl. ............................... 424/305; 260/468 H; 260/468 G; 260/477; 424/308
[58] Field of Search .......... 260/468 H, 468 G, 559 T; 424/305, 306

[56] References Cited

PUBLICATIONS

Chaphekar, J. Indian, Chem. Soc., 51(5), pp. 564–565 (1974).
Olin, Chem. Abst., 25:2708.
Albert, Chem. Abst. 9:1775.

Primary Examiner—James O. Thomas, Jr.
Assistant Examiner—Michael Shippen

[57] ABSTRACT

Certain carboxylic acid esters in which the alcohol portion contains an alpha-thioamide group are useful as pesticides.

11 Claims, No Drawings

THIOAMIDE PESTICIDES

FIELD OF THE INVENTION

The present invention relates to new thioamides, their preparation, their use as pesticides and to pesticidal compositions containing the thioamides.

BACKGROUND OF THE INVENTION

Pyrethroids, which are botanical insecticides derived from pyrethrum flowers, have long been used as pest control agents. Synthetic pyrethrin-like compounds have been produced over the years in attempts to duplicate the activity of natural pyrethrins. The compounds of the present invention are based on esters known to exhibit pyrethrin-like activity but are characterized by an alpha thioamide moiety in the alcohol portion. These new compounds have the desirable low order of toxicity to warm-blooded animals as well as rapid, knock-down action against insect pests characteristic of pyrethroids. In addition, the new compounds are highly persistent on foliage. They also have outstanding insecticidal, acaricidal and tickicidal properties. In view of these properties, the new thioamides are very suitable for use on food crops, household sprays, for stock and pet treatment, industrial sanitation and to protect stored food in warehouses.

SUMMARY OF THE INVENTION

The novel compounds of the present invention are thioamides having the formula

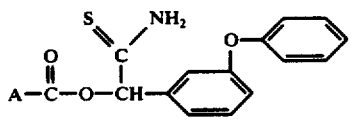

and salts thereof wherein A represents an optionally substituted cyclopropyl group or an optionally substituted benzyl group.

Preferably, A represents a cyclopropyl group of the formula (II)

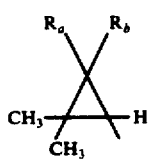

wherein $R_a$ and $R_b$ each represents an alkyl group of 1 to 6 carbon atoms, a halogen atom of atomic number 9 to 35 or $R_a$ and $R_b$ together represent an alkylene group of up to 6 carbon atoms or $R_a$ represents hydrogen and $R_b$ represents an alkenyl or haloalkenyl group of up to 6 carbon atoms or A represents an optionally substituted benzyl group of the formula (III)

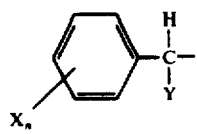

wherein X represents a halogen atom of atomic number 9 to 35, $n$ represents 0, 1, 2 or 3; and Y represents an alkyl group of up to 6 carbon atoms.

Good results can be obtained using a cyclopropyl group of the formula II wherein $R_a$ and $R_b$ each represents methyl or a chlorine atom; or $R_a$ and $R_b$ together represent an alkylene group of 3 carbon atoms; or $R_a$ represents hydrogen and $R_b$ represents an isobutenyl group or an haloalkenyl group having of from 2 to 6 carbon atoms and of from 1 to 3 chlorine or bromine atoms, especially a mono- or dichloro- vinyl group.

Good results can be obtained using a benzyl group of the formula III wherein X represents a chlorine atom; $n$ represents 0 or 1; and Y represents isopropyl.

Examples of particularly preferred thioamides according to the present invention are:
alpha-thioamido-3-phenoxybenzyl-2,2,3,3-tetramethyl cyclopropane carboxylate;
alpha-thioamido-3-phenoxybenzyl-2,2-dichlorovinyl-3,3-dimethyl cyclopropane carboxylate;
alpha-thioamido-3-phenoxybenzyl-2,2-dimethylvinyl-3,3-dimethyl cyclopropane carboxylate;
alpha-thioamido-3-phenoxybenzyl-2,2-dimethyl-3-spirocyclobutanecyclopropane carboxylate and
2-(4-chlorophenyl)-2-isopropylacetic acid, alpha-thioamido-3-phenoxybenzyl ester.

It should be noted that optical isomers, cis-trans isomers and other kinds of geometric isomers of the thioamides according to the general formula (I) are within the scope of the present invention as well as racemates and mixtures of isomers of one or more of the thioamides according to the general formula (I), especially tautomeric isothioamides.

The actual constitution of the thioamides is not yet known completely. Under some conditions they act as thioamides and under others as isothioamides. It is also possible that both forms exist simultaneously. The compounds according to the present invention form salts with acids or bases. It is probable that the salts are the salts of the isothioamides. The preferred salts are the alkali metal, especially sodium, ammonium and amine, especially di- and triethylamine and alkanolamine salts, salts of heterocyclic nitrogeneous bases, for example pyridine, and the mineral acid salts especially the hydrochlorides and hydrobromides.

The thioamides according to the present invention may be prepared by methods known in the art.

Suitable routes to the preferred thioamides include reacting the corresponding amide (compounds according to formula I wherein the carbon-sulphur double bond is a carbon-oxygen double bond) with phosphorus pentasulphide or a similar sulphurizing agent. Good results can be obtained by reacting the corresponding nitrile (compounds according to the general formula I wherein the group

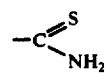

would be a $-C \equiv N$ group) with hydrogen sulphide in a dipolar aprotic solvent such as dimethylformamide or hexamethylene phosphorusamide in the presence of a basic catalyst. A particularly suitable method of carrying out this reaction comprises treating a solution of the nitrile in pyridine or an alcohol containing a strong nitrogeneous base, particularly a tertiary amine, for example triethylamine, or an alkanolamine, such as triethanolamine, with hydrogen sulphide. The reaction can be suitably carried out at room temperature. The solution is preferably saturated with hydrogen sulphide.

The thioamides according to the present invention have outstanding insecticidal, acaricidal as well as tickicidal properties. The invention therefore relates also to compositions comprising a carrier or a surface-active agent or both a carrier and a surface-active agent and at least one of the thioamides to be specified hereinafter.

The term "carrier" as used herein means a solid or fluid material, which may be inorganic or organic and of synthetic or natural origin, with which the active compound is mixed or formulated to facilitate its application to the plant, seed, soil or other object to be treated, or its storage, transport or handling.

The surface-active agent may be an emulsifying agent or a dispersing agent or a wetting agent; it may be non-ionic or ionic.

Any of the carrier materials or surface-active agents usually applied in formulating pesticides may be used in the compositions of the invention, and suitable examples of these are to be found, for example, in British patent specification No. 1,232,930.

The composition of the invention may be formulated as wettable powders, dusts, granules, solutions, emulsifiable concentrates, emulsions, suspension concentrates or aerosols. Wettable powders are usually compounded to contain 25, 50 or 75% of toxicant and usually contain, in addition to solid carrier, 3-10%w of a dispersing agent and, where necessary, 0-10%w of stabilizer(s) and/or additives, such as penetrants or stickers.

Dusts are usually formulated as a dust concentrate having a similar composition to that of a wettable powder but without a dispersant, and are diluted in the field with further solid carrier to give a composition usually containing ½-10%w of toxicant. Granules are usually prepared to have a size between 10 and 100 BS mesh (1.676 - 0.152mm), and may be manufactured by agglomeration or impregnation techniques. Generally, granules will contain ½-25%w toxicant and 0-10%w of additives such as stabilizers, slow release modifiers and binding agents. Emulsifiable concentrates usually contain, in addition to the solvent and, when necessary, co-solvent, 10-50%w/v toxicant, 2-20%w/v emulsifiers and 0-20%w/v of appropriate additives such as stabilizers, penetrants and corrosion inhibitors. Suspension concentrates are compounded so as to obtain a stable, non-sedimenting, flowable product and usually contain 10-75%w toxicant, 0.5-15%w of dispersing agents, 0.1-10%w of suspending agents such as protective colloids and thixotropic agents, 0-10%w of appropriate additives such as defoamers, corrosion inhibitors, stabilizers, penetrants and stickers, and as carrier, water or an organic liquid in which the toxicant is substantially insoluble; certain organic solids or inorganic salts may be dissolved in the carrier to assist in preventing sedimentation or as anti-freeze agents for water.

Aqueous dispersions and emulsions, for example compositions obtained by diluting a wettable powder or a concentrate according to the invention with water, also lie within the scope of the present invention. The said emulsions may be of the water-in-oil or of the oil-in-water type, and may have a thick 'mayonnaise'-like consistency.

The compositions of the invention may also contain other ingredients for example, other compounds possessing pesticidal, especially insecticidal, acaricidal, herbicidal or fungicidal properties.

EXAMPLES

The invention is further illustrated in the following examples which are for the purpose of illustration only and should not be regarded as limiting the invention in any way.

EXAMPLE I

Alpha-Thioamido-3-Phenoxybenzyl-2,2,3,3-Tetramethyl Cyclopropane Carboxylate

A stream of hydrogen sulphide gas was bubbled through a solution of alpha-cyano-3-phenoxybenzyl-2,2,3,3-tetramethyl cyclopropane carboxylate (5g) in dry dimethyl formamide (40ml) containing triethanolamine (2ml) at room temperature for 24 hours. The resultant red solution was poured into water (1 liter), extracted with ether and the ether extracts washed several times with water and dried over sodium sulphate. Evaporation of ether and crystallisation of the residue from toluene/hexane gave the desired product as a white solid m.p. 128°-9° C.

Analysis: Calculated for $C_{22}H_{25}NO_3S$: C68.9; H.6.6; N3.6%. Found: C69.2; H6.7; N3.5%.

EXAMPLES II-VI

Following procedures similar to that described in Example I, further compounds according to the invention were prepared. The physical characteristics and analyses are given in Table I.

The present invention relates also to a method for combatting insects and/or acarids and/or ticks by applying to a locus a thioamide according to the present invention or a composition comprising at least one thioamide according to the present invention.

EXAMPLES VI

Pesticidal Activity.

The insecticidal, acaricidal and tickicidal activity of the compounds according to the present invention was tested as follows:

I. A 1.0% by weight solution in acetone of the compound to be tested was prepared, and taken up in a micrometer syringe. Two to three-day old adult female house flies (*Musca domestica*) were anaesthetized with carbon dioxide, and 1 microliter drop of the test solution was brushed off on the ventral abdomen of each, 20 flies being treated. The treated flies were held for 24 hours in glass jars, each containing a little granulated sugar as food for the flies, and the percentage of dead and moribund individuals was then recorded.

II. The compounds were formulated as solutions or suspensions in water containing 20% by weight of acetone and 0.05% by weight of Triton X 100 as wetting agent. The formulations contained 0.7% by weight of the compound to be tested. Turnip and broad bean plants, trimmed to one leaf each, were sprayed on the under-surface of the leaf with the above formulation. Spraying was effected with a spraying machine delivering 450 liters per hectare, the plants passing under the spray on a moving belt. Ten adult 1-2 week-old mustard beetles (*Phaedon cochleariae*) were placed on the spraying leaf of each turnip plant and ten apterous (6-day-old) vetch aphids (*Megoura viciae*) were placed on the sprayed leaf of each broad bean plant. The plants were then enclosed in glass cyclinders fitted at one end with a muslin cap. Mortality counts were made after 24 hours.

III. In tests against glass house spider mites (*Tetranychus urticae*), leaf discs cut from French bean plants were sprayed in the manner described under II. 1 hour after spraying, the disc were inoculated with 10 adult mites. Mortality counts were made 24 hours after inoculation.

IV. The compounds were formulated as solutions or fine suspensions in water containing 20% by weight of acetone and 0.05% by weight of Triton D 100 as wetting agent. The formulations contained 0.6% by weight of the compound to be tested. Pairs of leaves are removed from broad bean plants and placed on filter paper inside plastic petri dishes. Immediately prior to testing ten larvae of the Egyptian cotton leafworm (*Spodoptera littoralis*) are transferred onto the leaves and allowed to settle down. Larvae and leaves are sprayed together using a spraying machine delivering 340 liters/hectare, operated under the conveyor belt principle. After spraying the larvae are covered with a petri dish lid. After 24 hours, the percentage of dead and moribund larvae was recorded.

V. The compounds were formulated as solutions or fine suspensions in acetone containing 10% by weight of polyethylene glycol having an average molecular weight of 400. The formulations contained 0.1% by weight of the compound to be tested. 1 ml of the above-mentioned solution is applied evenly to a filter paper situated inside a petri dish. After the paper is sufficiently dry it is folded in half and partly crimped along the outer edge to form a packet. About 80–100 larval ticks (*Boophilus microplus*) are transferred into the packet which is then sealed completely. The packets are placed inside an incubator, maintained at 27° C and 80% relative humidity, before assessing mortality 24 hours later.

The result of these tests are shown in Table 2 in which A denotes complete kill, B some kill and C no kill of the test species.

We claim:

1. A thioamide derivative of the formula

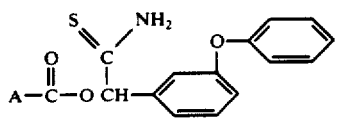

wherein A represents a cyclopropyl group of the formula

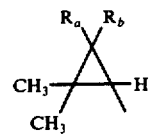

wherein $R_a$ and $R_b$ individually represents an alkyl group of 1 to 6 carbon atoms, a halogen atom of atomic number 9 to 35 or $R_a$ and $R_b$ together represent an alkylene group of up to 6 carbon atoms or $R_a$ represents hydrogen and $R_b$ represents an alkenyl or haloalkenyl group of up to 6 carbon atoms.

2. A thioamide derivative according to claim 1 wherein A is a substituted cyclopropyl group in which $R_a$ and $R_b$ each represents methyl or chlorine or $R_a$ and $R_b$ together represent an alkylene group having of 3 carbon atoms, or $R_a$ represents hydrogen and $R_b$ represents an isobutenyl or an haloalkenyl group having of from 2 to 6 carbon atoms and from 1 to 3 chlorine or bromine atoms.

3. A thioamide derivative according to claim 2 wherein $R_a$ and $R_b$ each represents methyl.

4. A thioamide derivative according to claim 2 wherein $R_a$ represent hydrogen and $R_b$ represents isobutenyl.

5. A thioamide derivative according to claim 2 wherein $R_a$ represents hydrogen and $R_b$ represents dichlorovinyl.

6. A thioamide derivative as claimed in claim 2 wherein $R_a$ and $R_b$ together represent an alkylene group of 3 carbon atoms.

7. An insecticidal or acaricidal composition comprising an insecticidally or acaricidally effective amount of a thioamide as claimed in claim 1 and at least one carrier or surface-active agent.

8. A method of combatting insect or acarid pests which comprises applying to the pest or to the locus thereof a pesticidally effective amount of a thioamide as claimed in claim 1 or a composition thereof.

9. A method as claimed in claim 8 wherein the insect pest is of the species *Musca domestica*.

10. A method as claimed in claim 8 wherein the insect pest is of the species *Spodoptera littoralis*.

11. A method as claimed in claim 8 wherein the insect pest is of the species *Megoura viciae*.

Table 1

| Example | Compound | m.p or b.p° C | Analysis | |
|---|---|---|---|---|
| II | -(4-chlorophenyl)-2-alpha-thioamido-3-phenoxybenzyl ester | brown glue | Calculated for $C_{25}H_{24}ClNO_3S$ Found | C66.2;H5.3;N3.1% C66.3;H5.2;N2.8% |
| III | alpha-thioamido-3-phenoxybenzyl-2,2-dichloro-vinyl-3,3-dimethylcyclopropane carboxylate | yellow-green glue | Calculated for $C_{22}H_{21}Cl_2NO_3S$ Found | C58.7;H4.7;N3.1% C58.7;H4.8;N3.0% |
| IV | alpha-thioamido-3-phenoxybenzyl-2,2-dimethyl-vinyl-3,3-dimethylcyclopropane carboxylate | brown glue | Calculated for $C_{24}H_{27}NO_3S$ Found | C70.4;H6.6;N3.4% C70.4;H6.6;N3.0% |
| V | alpha-thioamido-3-phenoxybenzyl-2,2-dimethyl-3-spirocyclobutane-cyclopropane carboxylate | colourless oil | Calculated for $C_{22}H_{25}NO_3S$ Found | C69.8;H6.4;N3.5% C69.7;H6.6;N3.1% |
| VI | 2-(3-chlorophenyl)-2-isopropylacetic acid, alpha-thioamide-3-phenoxybenzyl ester | oil | Calculated for $C_{25}H_{24}ClNO_3S$ Found | C66.2;H5.3;N3.1% C66.9;H5.2;N3.0% |

Table 2

| Compound of Example | Pesticidal Activity | | | | | |
|---|---|---|---|---|---|---|
| | M.d. | P.c. | S.l. | M.v. | T.u. | B.m. (larvae) |
| I | A | B | A | A | C | A |
| II | A | B | A | A | C | B |
| III | A | A | A | A | C | C |
| VI | A | A | A | A | B | C |